United States Patent [19]

Millerd

[11] Patent Number: 4,734,092
[45] Date of Patent: Mar. 29, 1988

[54] AMBULATORY DRUG DELIVERY DEVICE
[75] Inventor: Donald L. Millerd, San Diego, Calif.
[73] Assignee: IVAC Corporation, San Diego, Calif.
[21] Appl. No.: 15,931
[22] Filed: Feb. 18, 1987
[51] Int. Cl.$^4$ ............................................. A61M 31/00
[52] U.S. Cl. ..................................... 604/67; 604/140; 604/151; 128/DIG. 12
[58] Field of Search ............... 604/131, 140, 145, 151, 604/65, 67, 890, 891; 128/DIG. 12, DIG. 13; 222/389

[56] References Cited

U.S. PATENT DOCUMENTS

| | | | |
|---|---|---|---|
| 2,168,437 | 8/1939 | Buercklin | 604/143 |
| 3,951,147 | 4/1976 | Tucker et al. | |
| 4,395,259 | 7/1983 | Prestele et al. | 604/67 |
| 4,525,164 | 6/1985 | Loeb et al. | |
| 4,552,561 | 11/1985 | Eckenhoff et al. | |
| 4,626,244 | 12/1986 | Reinicke | 604/141 |

*Primary Examiner*—Stephen C. Pellegrino
*Attorney, Agent, or Firm*—Fulwider, Patton, Rieber, Lee & Utecht

[57] ABSTRACT

A device for infusing a drug into an ambulatory patient, the drug being contained in a transparent spiral conduit which is embedded in a disposable flexible casting conformingly adhered to the patient's body, includes a reusable micropump module which is detachably mounted in a collar valve on the casting and forces oxygen into the conduit under pressure to expel the drug into a semi-pivoting cannula inserted into the patient's body. A colored oil drop between the oxygen and the drug in the conduit provides a visual indication of drug quantity, while a filter with hydrophobic and hydrophylic membranes keeps the oxygen and oil substantially out of the cannula. A test button sounds an alarm when the device is ready for use and a pressure sensitive switch automatically sounds an alarm and shuts off the pump if the drug becomes completely discharged from the conduit or if the drug delivery system becomes occluded and an interlock switch completes the circuit between the pump and a power source when the reusable module and disposable casting are joined.

26 Claims, 7 Drawing Figures

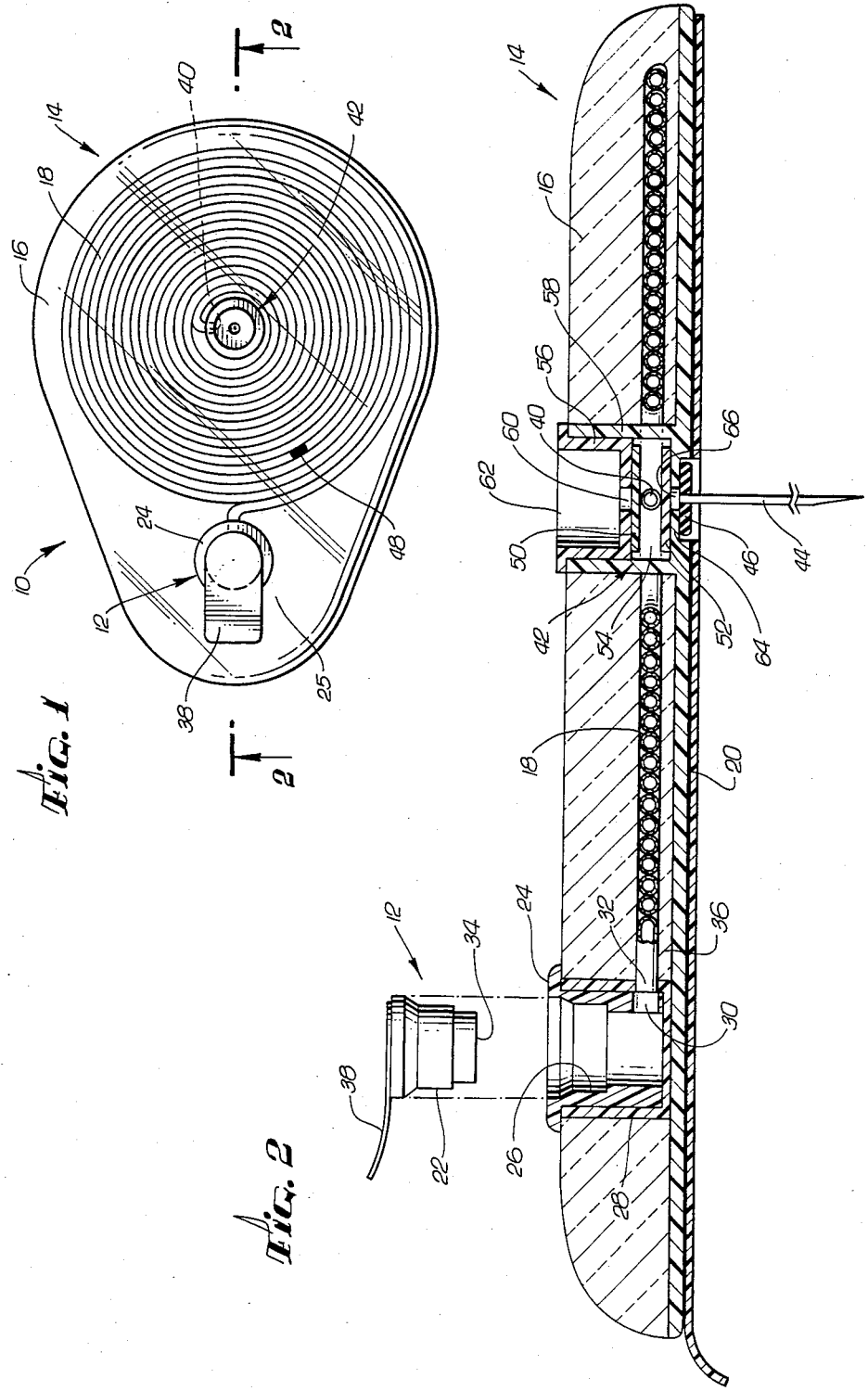

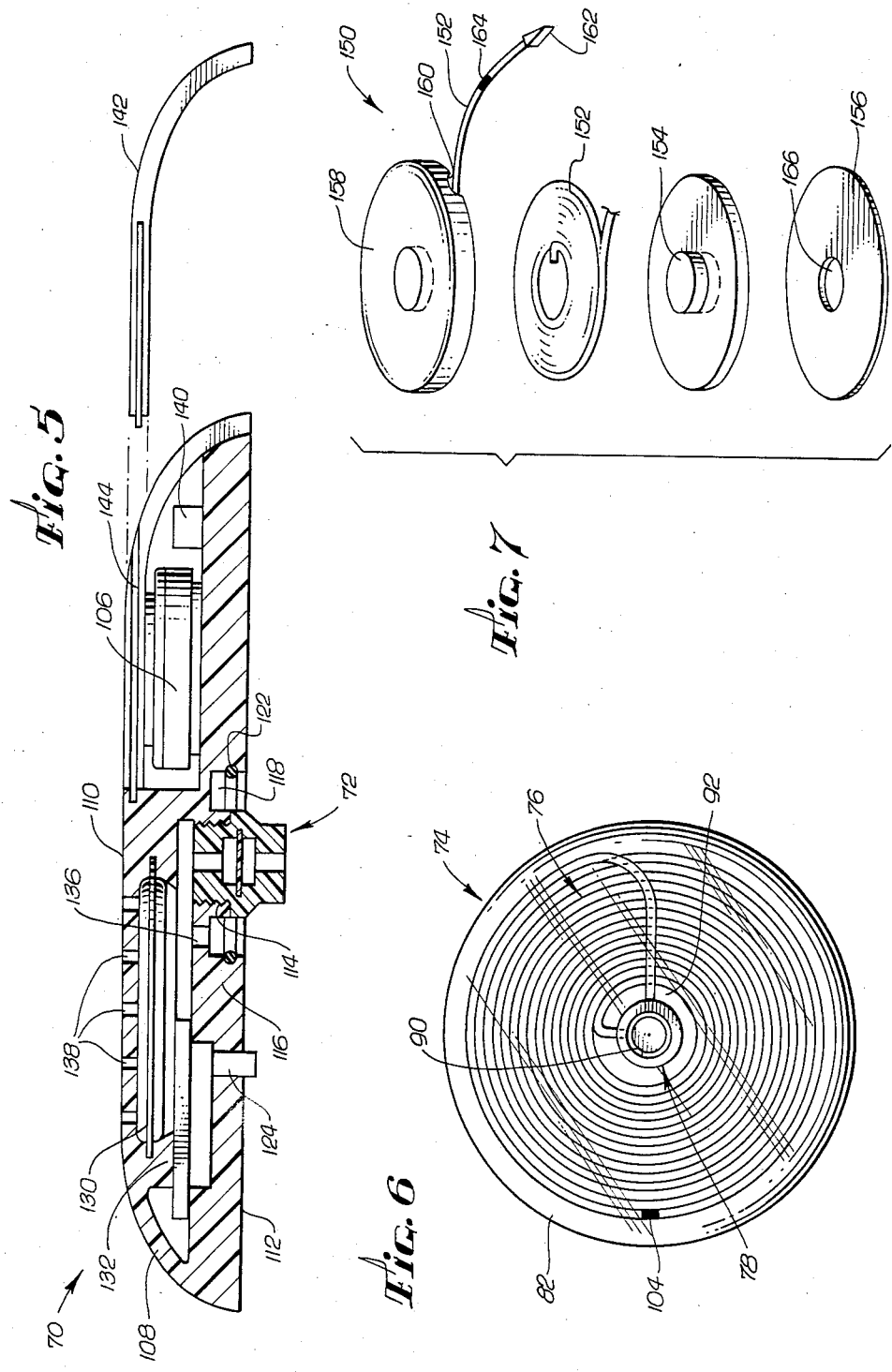

AMBULATORY DRUG DELIVERY DEVICE

BACKGROUND OF THE INVENTION

This invention relates generally to fluid delivery devices, and more particularly, has reference to a new and improved device for infusing a drug into an ambulatory patient.

In various clinical situations, the indicated procedure for treating the patient is to administer drugs or other pharmaceutical fluids into his body in a sustained manner over a substantial period of time. Fluids administered in this manner include liquid nutrients, blood, plasma, insulin and hormones.

A simple method for treating the patient in the above manner is to give him repeated bolus injections at various times. That procedure subjects the patient to discomfort and anxiety and also exposes him to the risk of undesirable side effects due to wide fluctuations in the amount of drug in his body at any one time. Furthermore, it demands either the time-consuming process of sterilizing reusable syringes after each injection or the expensive process of using a plurality of disposable syringes. It is also inconvenient for ambulatory patients who return to the physician's office each time an injection is needed.

The intravenous administration set, which includes the familiar bottle suspended above the patient, was developed to overcome some of the problems associated with bolus injections. Unfortunately, the IV set restricts mobility to the extent that it is not well-suited for use with an ambulatory patient.

Other methods for the gradual administration of drugs have been devised to eliminate the need for suspending the drug above the patient and thereby provide him with greater mobility. Mechanical pump dispensers use various types of mechanical pumps to expel the drug from a reservoir. Charged reservoir dispensers store a drug under pressure in a flexible reservoir and then selectively expel that drug by the force of an internal reservoir pressure, the rate of release often being regulated by various valves. Pressurized gas dispensers use a pressurized gas to expel the drug. Osmotic dispensers rely on a solute that exhibits an osmotic pressure gradient against water to dispense the drug.

While the aforedescribed fluid administration techniques have served their purpose, there remains a continuing desire for further improvement therein.

The development of the fluid delivery micropump, described in commonly assigned, co-pending application Ser. No. 016,019, filed by Henri J. R. Maget and Paul Krejci and entitled "Fluid Delivery Micropump", was a major step forward. It overcomes many of the problems associated with the existing devices by providing a self-powered prime mover module which is compact, economical, simple in structure and easy to operate, and which is useful in a micropump capable of delivering a constant flow of fluid at relatively low rates. The pump is sufficiently small and lightweight to be worn by an ambulatory patient and its simple structure makes it easy to use and operate.

Briefly, the prime mover module includes a housing, an electrolytic membrane disposed in the housing and having first and second membrane surfaces, a first material-pervious electrode disposed on the first membrane surface and a second material-pervious electrode disposed on the second membrane surface, an electrical power source, preferably a zinc-air battery, disposed in the housing for establishing a voltage gradient across the electrolytic membrane when exposed to the atmosphere, one or more ports in the housing to establish communication between the battery and the atmosphere, the voltage gradient across the membrane ionizing oxygen at the first material-pervious electrode, transporting the ions through the electrolytic membrane to the second-material pervious electrode, and reconverting the ions to molecules of oxygen which are evolved at the second-material pervious electrode. Removable sealing means close the ports to inactivate the battery. A more detailed description of the structure and function of the device is contained in the referenced patent application, the entire disclosure of which is incorporated herein by reference.

The fluid delivery micropump has many advantages and is particularly well suited for use in satisfying the continual desire for new and improved ambulatory drug delivery devices which are less bulky and conspicuous, more comfortable to wear and more economical. A further need exists for improvements in ambulatory drug delivery devices to make it easier to determine the amount of drug contained in the device and the amount of drug infused into the patient, to make it easier to determine whether the device is operating properly, to enhance user comfort, to promote filtration capabilities and to facilitate proper operation. The present invention fulfills all of these needs.

SUMMARY OF THE INVENTION

Briefly, and in general terms, the present invention provides an economical and reliable low-profile fluid delivery device which is easy to use and inexpensive to manufacture, which can be worn inconspicuously and comfortably under the clothing of an ambulatory patient to provide him with a continuous infusion of a drug or other fluid at a specified constant rate over an extended period of time, which filters the fluid delivered, and which provides a ready indication of drug levels and operational conditions.

In a presently preferred embodiment, by way of example and not necessarily by way of limitation, the ambulatory drug delivery device includes an extended fluid conduit, preferably a spiral tube which acts as a reservoir for a drug. The conduit is embedded in a flexible casting which is adhered to the patient's body. The casting conforms to the contours of the patient's body and flexes as he moves, thus providing a comfortable fit.

A prime mover module, incorporating the recently developed fluid delivery micropump described above, is mounted on the casting to draw in atmospheric oxygen and force it into the conduit under pressure. The oxygen expels the drug from the conduit and drives it into a cannula which is inserted into the patient's body. The drug passes through the cannula and infuses into the patient. The cannula is pivotably mounted to the casting to enhance comfort about the injection site.

Preferably, the conduit is made of transparent material and contains an indicator, preferably a colored oil drop, positioned between the pressurized oxygen and the drug. The drop moves along the conduit as the drug is expelled to provide a visual indication of the amount of drug remaining in the conduit and the amount of drug infused into the patient. A filter with hydrophylic and hydrophobic membranes at the end of the conduit keeps the pressurized oxygen and the oil drop substantially out of the cannula.

In one embodiment of the invention, the device has a pressure sensitive switch which automatically sounds respective "empty" and "clogged" alarms should the drug become completely discharged from the conduit or should the drug delivery system become occluded. The switch is sensitive to the abrupt change in pressure which would occur in the conduit if the supply of drug was exhausted or the system had occluded. The device may also have a test button which actuates a second pressure sensitive switch and sounds a "ready" alarm when the pressure in the conduit is at normal operating level.

The casting and the pump module can be provided as a single, integrated unit or they can be provided as separate, detachable units. Detachable units are preferred because they permit the more expensive pump module to be reused with a plurality of less expensive, disposable castings. The pump module may be mounted in a collar valve on the casting to provide enhanced on/off and fill/re-fill capabilities. An interlock switch completes the circuit between the pump and the power source when the detachable units are joined.

These and other objects and advantages of the invention will become apparent from the following more detailed description, when taken in conjunction with the accompanying drawings of illustrative embodiments.

DESCRIPTION OF THE DRAWINGS

FIG. 1 is a top plan view of an ambulatory drug delivery device embodying features of the present invention;

FIG. 2 is an enlarged side view of the device of FIG. 1 with the pump module shown separated from the reservoir module and with the reservoir module being shown in section taken substantially along the line 2—2 of FIG. 1;

FIG. 5 is an enlarged sectional view, taken substantially along the line 5—5 in FIG. 4;

FIG. 6 is a reduced top plan view of the reservoir module shown in FIG. 3;

FIG. 7 is an exploded view of yet another embodiment of the present invention.

DETAILED DESCRIPTION OF THE PREFERRED EMBODIMENTS

Figure 3:
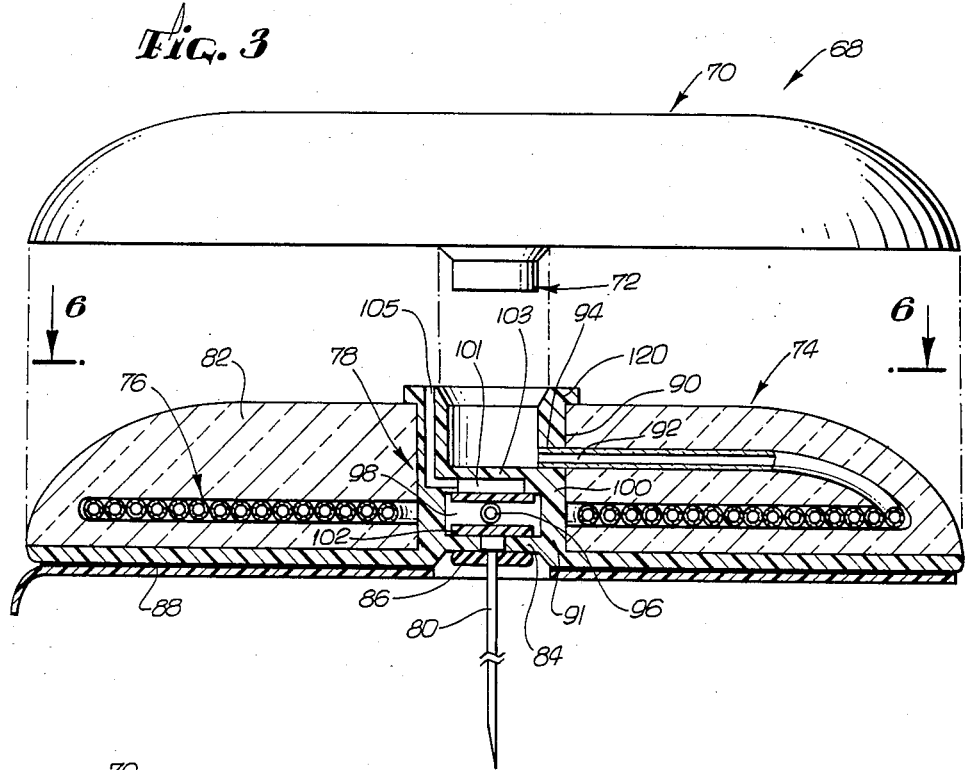
FIG. 3 is a side elevational view of another embodiment of the present invention, showing a pump module separated from a reservoir module and showing the reservoir module substantially in cross-section.

As shown in the drawings for purposes of illustration, and with particular reference to FIG. 1, the present invention is embodied in an ambulatory drug delivery device, indicated generally by the numeral 10, which administers a gradual infusion of a drug into the body of a patient at a relatively constant, low rate. The device 10 includes a pump module, indicated generally by the numeral 12, and a reservoir module, indicated generally by the numeral 14.

The reservoir module 14 includes a flexible housing 16 having an internal fluid conduit passageway 18. The conduit 18 is preferably provided in the form of a spiraled flexible tube which is embedded in the silastic rubber casting forming the housing 16. As shown in FIG. 2, an adhesive surface 20 is provided along the bottom of the reservoir module 14 for attaching the module 14 to a patient's body. The flexible nature of the housing 16 and conduit 18 allows the module 14 to conform to the contours of the patient's body and accommodate his movements with comfort.

The pump module 12 is generally identical to the prime mover module of the recently developed fluid delivery micropump discussed above. As shown in FIG. 2, the module 12 has a generally cylindrical body 22 which is removably received in a collar valve 24 mounted on a side extension 25 of the reservoir module 14. The collar valve 24 has an inner sleeve 26 preferably formed of elastomeric material which intimately engages the body 22 to secure the module 12 in place. The inner sleeve 26 is rotatably mounted in a stationary outer sleeve 28 sealed into the reservoir module housing 16. Rotation of the inner sleeve 26 selectively aligns a radial port 30 formed therein within a radial port 32 formed in the outer sleeve 28 to vent the pressurized oxygen evolved from the outlet end 34 of the pump module 12. The inlet end 36 of the conduit 18 is connected to the port 32 so that the vented oxygen is forced into the conduit 18 where it acts as a driving fluid.

In the embodiment of FIGS. 1 and 2, the pump module 12 is self-powered by an internal zinc-air battery (not shown) which is activated by removing a peel tab 38 covering air inlet ports (not shown) in the top of the module 12. However, it is understood that it may be desirable to provide an electro-mechanical on/off switch either as an auxiliary activating device or as the primary activating device, particularly where a different type of battery is used. Such a switch may be operatively connected to the collar valve 24 so that it is actuated when the inner sleeve 26 is rotated to align the ports 30 and 32.

The drug to be infused into the patient's body is contained in the conduit 18 which acts as a fluid reservoir. The pressurized oxygen introduced into the inlet end 36 of the conduit 18 drives the drug and expels it from the outlet end 40 of the conduit 18. The expelled drug passes through a filter 42 into a cannula 44 which enters the patient's body when the reservoir module 14 is adhered to his skin. The cannula 44 infuses the drug into the patient. The cannula 44 is semi-pivotably mounted on the reservoir housing 16 by an elastomeric seal 46 to promote patient comfort around the cannula injection site.

As shown in FIG. 1, a slug 48 of oil placed in the conduit 18 acts as a movable indicator positioned between the pressurized oxygen and the drug. The slug 48 moves through the conduit 18 as the drug is expelled so that the position of the slug 48 at any given time provides a ready indication of the amount of drug in the conduit 18 and the amount of drug infused into the patient. The slug is preferably dyed to a different color than the drug and the conduit 18 and housing 16 are preferably made sufficiently transparent so that the position of the slug 48 can be easily determined by an external visual inspection of the device 10.

As best shown in FIG. 2, the filter 42 includes a hydrophobic membrane 50 and a hydrophylic membrane 52 on opposite sides of a fluid chamber 54 which receives the drug expelled from the outlet end 40 of the conduit 18. The hydrophobic membrane 50 is mounted on the end of a retainer 56 inserted into a housing sleeve 58 which receives the outlet end 40 of the conduit 18. An axial port 60 in the retainer 56 vents the fluid chamber 54 into a void 62 exposed to the atmosphere. The hydrophylic membrane 52 is mounted on a recessed wall 64 of the housing 16 which supports the cannula mount 46. An axial port 66 in the wall 64 vents the fluid chamber 54 into the interior axial bore (not shown) extending the length of the cannula 44. The filter 42 is located slightly off-center of the reservoir module housing 16. The membranes may be formed of any of various materials, such as polyethylene.

The hydrophobic membrane 50 is substantially impervious to liquids but substantially pervious to gas, while the hydrophylic 52 is substantially pervious to liquids but substantially impervious to gas. Hence, any gas in the chamber 54 is substantially vented to the atmosphere through the hydrophobic membrane 50 and port 60 while the liquids, i.e., the drugs, are substantially vented into the cannula 44 through the hydrophylic membrane 52 and port 66. The filter 42 keeps oxygen out of the patient's body should the pump 12 continue to drive oxygen through the conduit 18 after a supply of the drug is exhausted. The filter 42 also removes gas bubbles from the drug.

The hydrophylic membrane 52 has a limited porosity so that it is substantially impervious to the oil slug 48 which generally has a higher viscosity than the drug. The filter 42 thus prevents the oil slug 48 from contaminating the drug infused into the patient's body.

The device 10 shown FIGS. 1 and 2 is semidisposable. The pump module 12 can be detached from the reservoir module 14 and reused with other or different reservoir modules. The reservoir module 14, on the other hand, is a disposable unit intended for one-time use. The drug and all the components in contact with the drug and the patient's body are contained in the disposable reservoir module 14.

The drug delivery device 10 can be furnished in two ways. The conduit 18 can be pre-filled with the drug and the pump module 12 can be pre-inserted into the collar valve 24. One need only attach the device 10 to the patient's body, remove the peel tab 38 and rotate the valve sleeve 26 to intiate treatment. On the other hand, the device 10 may be furnished with an empty reservoir 18 and a detached pump module 12. In that case, the valve 24 must be opened by rotating the sleeve 26, the system purged by injecting a drug into the conduit 18 via the valve 24, the valve 24 closed by again rotating the inner sleeve 26, and the pump module 12 then pressed into the valve sleeve 26. The device 10 is used in the same manner as before, namely, by attaching it to the patient's body, removing the peel tab 38 and rotating the valve sleeve 26.

An alternative embodiment of a drug delivery device incorporating features of the present invention is shown in FIGS. 3-6 and indicated generally by the numeral 68. The device 68 has a two-part housing, i.e., a reusable portion 70 containing the pump module 72 and a disposable portion 74 containing the spiral fluid reservoir 76, the filter 78 and the semi-pivoting cannula 80.

The disposable portion 74, best shown in FIGS. 3 and 6, is substantially similar to the reservoir module 14 shown in FIGS. 1 and 2 except that the pump module mount, the filter and the cannula are all centrally located. The fluid reservoir 76 is provided by a transparent, flexible tube embedded in a transparent, flexible, silastic casting 82. The cannula 80 is mounted on a recessed wall 84 of the casting by an elastomeric seal 86 and is surrounded by an adhesive surface 88 which attaches the casting 82 to the patient's body. The filter 78 is substantially similar in structure and function to the filter 42 shown in FIG. 2 in all but two respects. First, the inner wall of the retainer 90 is formed integrally with the sleeve 91 and is shaped to conformingly receive the pump module 72 in a manner similar to the inner sleeve 26 of the collar valve 24. Second, a space 101 is provided between the hydrophobic membrane 100 and the adjacent retainer wall 103 from which the axial port has been eliminated. The inlet end 92 of the spiral tube 76 is connected to a radial port 94 in the retainer 90 to direct oxygen from the pump 12 into the tube 76. The outlet end 96 of the tube 76 is connected to the filter 78 and vents into a chamber 98 between the hydrophobic membrane 100 and the hydrophylic membrane 102 in a manner substantially identical to that shown in FIG. 2. A dyed oil slug 104 positioned in the tube 76 between the drug and the pressurized oxygen provides a visual indication of the amount of drug in the tube 76 and the amount of drug infused into the patient, all in manner substantially identical to the slug 48 shown in FIG. 1.

The pump module 72 is substantially similar to the pump module 12 shown in FIG. 2 with the exception that the self-contained, air-actuated battery used in the module 12 has been replaced by a conventional external battery 106. That difference makes it unnecessary for the module 72 to have a peel tab actuator.

Figure 4:
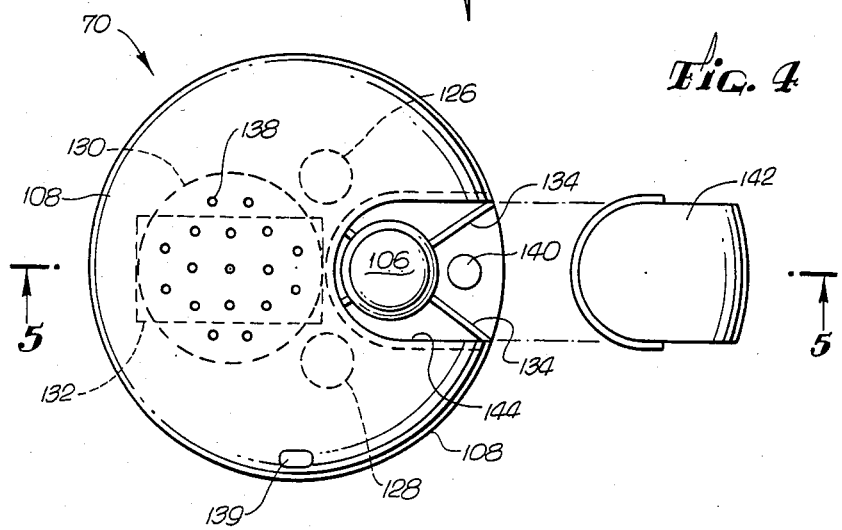
FIG. 4 is a partially exploded reduced top plan view of the pump module shown in FIG. 3.

Details of the reusable portion 70 of the device 68 are best shown in FIGS. 4 and 5.

The reusable portion 70 includes a housing 108 having a generally dome-shaped cap 110 and a flat base 112 configured to rest atop the casting 82 when the two portions 70 and 74 are joined by inserting the pump module 72 into the retainer 90. The pump module 72 is detachably connected to the base 112 by a screw thread connection 114 and draws atmospheric oxygen through holes 138 in the cap 110. An annular collar 116 concentrically spaced about the pump 72 forms an annular space 118 which is placed in fluid communication with the space 101 between the hydrophobic membrane 100 and the retainer wall 103 via an axial passageway 105 through the retainer 90 when the portions 70 and 74 are joined. An annular lip 120 on the end of the retainer 90 enters the space 118 and seats against an annular seal 122 mounted in the collar 116. A push-button type on/off switch 124 mounted in the base 112 is automatically switched from the "off" position to the "on" position when the base 112 is brought into contact with the casting 82 as the two portions 70 and 74 are joined. In the "on" position, the switch 124 closes the electrical circuit between the pump 72 and battery 106 to activate the pump 72. A pair of pressure sensitive switches 126 and 128, a piezo crystal 130 and an integrated circuit 132 are mounted on the base 112 and electrically interconnected. Power is supplied by the battery 106 which is removably held on the base 112 by retainers 134. Ports 136 formed in the base 112 adjacent the annular space 118 allow the switches 126 and 128 to sense the fluid pressure at the outlet 96 of the fluid reservoir 76.

One of the switches 126 is adjusted to turn "on" when the sensed outlet pressure falls outside predetermined levels indicative of an occlusion in the tube 76, filter 78 or cannula 80 or complete discharge of the drug from the tube 76. In the "on" state, the switch 126 sends a signal to the circuit 132 which activates the crystal 130 and causes it to produce an audible tone heard through the holes 138 in the cap 110. The tone provides a warning that the device 68 has stopped delivering drug.

When the crystal 130 produces the alarm tone, it drains so much power that the battery 106 becomes unable to drive the pump 72 and the pump 72 thus automatically shuts down.

The other switch 128 is adjusted to turn "on" when the sensed outlet pressure is within a normal operating range. A normally-open push-button switch 139 in the circuit between the pressure sensitive switch 128 and the integrated circuit 132 acts as a "test" button. If the button 139 is depressed when the pressure sensitive switch 128 is "on", the crystal 130 will produce a tone. If the switch 128 is "off", no tone is produced. The presence of a tone when the button 139 is depressed thus indicates that the system is operating at normal pressure and is ready for use. The "ready" tone ceases immediately upon release of the button 139 to prevent a drain on the battery 106.

A potentiometer 140 mounted on the base 112 is electrically connected into the circuit between the battery 106 and the pump 72. By controlling the amount of current passing through the pump 72, the potentiometer controls the rate at which oxygen is transported through the pump and consequently the rate at which fluid is expelled from the reservoir 76. The potentiometer 112 and battery 106 are located under a removable cover 142 which fits into a notch 144 in the cap 110.

Another embodiment of the invention is the ambulatory drug delivery device 150 shown in FIG. 7 which is particularly easy to manufacture.

The tube reservoir 152 is coiled around a pump module 154 which is positioned in the center of a rigid plastic base 156. A housing 158 fits over the module 154 and tube 152 and attaches to the base 156. The outlet end of the tube 152 extends through an opening 160 in the side wall of the housing 158. An air eliminating filter 162 is attached to the outlet end of the tube 152 and an oil slug indicator 164 is positioned in the tube 152. The inlet end of the tube 152 communicates with a fill port 166 in the base 156.

From the foregoing, it will be appreciated that the ambulatory drug delivery device of the present invention is economical and reliable, can be worn inconspicuously and comfortably under the clothing of an ambulatory patient, effectively filters the drug delivered and provides a ready indication of drug levels and operational conditions.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. Ambulatory drug delivery apparatus, comprising:
   a housing;
   a fluid reservoir in said housing comprising an extended conduit adapted for storing a fluid to be delivered and having an inlet end and an outlet end,
   pump means in communication with said inlet end for pressurizing a driving fluid and introducing said pressurized driving fluid into said conduit;
   fluid delivery means in communication with said outlet end for delivering fluid from said conduit upon said introduction of pressurized driving fluid;
   movable indicator means disposed in said conduit between said driving fluid and said fluid to be delivered; and
   attachment means for attaching said housing to a user's body.

2. Apparatus as set forth in claim 1, wherein said indicator means comprises an oil slug colored differently from at least one of said fluids.

3. Apparatus as set forth in claim 1, wherein said conduit is sufficiently transparent to permit visual observation of fluids therein.

4. Apparatus as set forth in claim 1, wherein said conduit comprises a spiraled flexible tube.

5. Ambulatory fluid delivery apparatus, comprising:
   a housing;
   spiral passageway means in said housing for carrying a fluid to be delivered, said passageway means having an inlet and an outlet;
   pump means in communication with said inlet for pressurizing a driving fluid and introducing said pressurized driving fluid into said passageway means;
   fluid delivery means in communication with said outlet for delivering fluid from said passageway means upon said introduction of pressurized driving fluid; and
   attachment means for attaching said housing to a user's body.

6. Apparatus as set forth in claim 5, wherein said housing is flexible.

7. Apparatus as set forth in claim 6, wherein said housing comprises a flexible casting and said passageway means comprises a spiraled flexible tube embedded in said casting.

8. Apparatus as set forth in claim 5, wherein said pump means comprises a module detachably mounted on said housing.

9. Apparatus as set forth in claim 8, further comprising a rotatable collar valve mounted on said housing for receiving said module and for selectively opening and closing said communication between said pump means and said inlet.

10. Apparatus as set forth in claim 9, further comprising switch means for selectively activating said pump means, said collar valve being operatively connected to said switch means for operating said switch means upon rotation of said valve.

11. Apparatus as set forth in claim 5, wherein said pump means comprises:
    a pump housing;
    means for introducing atmospheric oxygen into said housing;
    an electrolytic membrane disposed in said housing and having first and second membrane surfaces;
    a first material-pervious electrode disposed on said first membrane surface and a second material-pervious electrode disposed on said second membrane surface; and
    an electrical power source disposed in said housing for establishing a voltage gradient across said electrolytic membrane to ionize said oxygen at said first material-pervious electrode, transport said ions through said electrolytic membrane to said second material-pervious electrode, and reconvert said ions to molecules of oxygen which are evolved at said second material-pervious electrode as said driving fluid.

12. Apparatus as set forth in claim 11, wherein said electrical power source comprises a zinc-air battery.

13. Apparatus as set forth in claim 12, further comprising at least one port formed in said pump housing to establish communication between said battery and the atmosphere, and wherein removable sealing means are provided for closing said port.

14. Apparatus as set forth in claim 5, wherein said fluid delivery means comprises a cannula pivotably mounted on said housing.

15. Apparatus as set forth in claim 5, wherein said attachment means comprises an adhesive surface on said housing.

16. Ambulatory fluid delivery apparatus, comprising:
a housing;
passageway means in said housing for carrying a fluid to be delivered, said passageway means having an inlet and an outlet;
pump means in communication with said inlet for pressurizing a driving fluid and introducing said pressurized driving fluid into said passageway means;
fluid delivery means in communication with said outlet for delivering fluid from said passageway means upon said introduction of pressurized driving fluid;
attachment means for attaching said housing to a user's body; and
filter means in communication with said outlet for preventing gas in said passageway means from entering said fluid delivery means, said filter means comprising;
a fluid chamber in communication with said outlet for receiving fluid from said passageway means upon said introduction of pressurized driving fluid;
a first outlet port establishing communication between said chamber and the atmosphere and a second outlet port establishing communication between said chamber and said fluid deliver means;
a hydrophobic membrane disposed across said first outlet port for venting gas from said chamber into said atmosphere and retaining liquid in said chamber; and
a hydrophylic membrane disposed across said second outlet port for retaining gas in said chamber and venting liquid from said chamber into said fluid delivery means.

17. Apparatus as set forth in claim 16, further comprising an oil slug disposed in said passageway means between said driving fluid and said fluid to be delivered, said oil slug having a different viscosity than said fluid to be delivered, said hydrophylic membrane being substantially impervious to fluid having said different viscosity.

18. Apparatus set forth in claim 16, wherein said fluid to be delivered comprises pharmaceutical material and said driving fluid comprises oxygen.

19. Ambulatory fluid delivery apparatus, comprising;
a housing having a disposable portion and a reusable portion detachably connected thereto;
passageway means in said disposable portion for carrying a fluid to be delivered, said passageway means having an inlet and an outlet;
pump means in said reusable portion in communication with said inlet for pressurizing a driving fluid and introducing said pressurized driving fluid into said passageway means;
fluid delivery means in said disposable portion in communication with said outlet for delivering fluid from said passageway means upon said introduction of pressurized driving fluid;
attachment means for attaching said housing to a user's body;
power source means for supplying electrical power to said pump means; and
switch means electrically connected to said power source means and said pump means for selectively establishing electrical communication therebetween, said switch means being mounted on said reusable portion and being configured to establish said electrical communication when said reusable portion is connected to said disposable portion.

20. Apparatus as set forth in claim 19, wherein said pump means is detachably connected to said reusable portion.

21. Ambulatory fluid delivery apparatus, comprising:
a housing;
passageway means in said housing for carrying a fluid to be delivered, said passageway means having an inlet and an outlet;
pump means in communication with said inlet for pressurizing a driving fluid and introducing said pressurized driving fluid into said passageway means;
fluid delivery means in communication with said outlet for delivering fluid from said passageway means upon said introduction of pressurized driving fluid;
attachment means for attaching said housing to a user's body; and
pressure sensor means operatively connected to said pump means for inactivating said pump means upon sensing pressure outside predetermined levels, said pressure sensor means being in communication with said passageway means for sensing fluid pressure therein.

22. Apparatus as set forth in claim 21, wherein said pressure sensor means comprises a pressure sensitive switch.

23. Apparatus as set forth in claim 21, further comprising alarm means operatively connected to said pressure sensor means for producing a warning signal upon said sensing of pressure outside predetermined levels.

24. Apparatus as set forth in claim 23, wherein said pump means and said alarm means are powered by a common battery, said battery being drained when said alarm means produces said warning signal, thereby inactivating said pump means.

25. Apparatus as set forth in claim 23, wherein said alarm means comprises a piezo crystal.

26. Apparatus as set forth in claim 21, further comprising pressure sensor means in communication with said passageway means for sensing said fluid pressure therein, alarm means operatively connected to said pressure sensor means for producing a warning signal when said pressure sensor means senses pressure within a predetermined range, and switch means operatively connected to said pressure sensor means for selectively activating said pressure sensor means.

* * * * *

UNITED STATES PATENT AND TRADEMARK OFFICE
CERTIFICATE OF CORRECTION

PATENT NO. : 4,734,092

DATED : March 29, 1988

INVENTOR(S) : Donald L. Millerd

It is certified that error appears in the above-identified patent and that said Letters Patent is hereby corrected as shown below:

In Col. 2, Line 28, after "invention" delete -- fulfulls -- and insert -- fulfills --.

In Col. 5, Line 28, after "shown" insert -- in --.

In Col. 5, Line 41, after "to" delete -- intiate -- and insert -- initiate --.

In Claim 1, Col. 7, Line 59, after "outlet end" delete -- , -- and insert -- ; --.

In Claim 16, Col. 9, Line 35, after "fluid" delete -- deliver -- and insert -- delivery --.

Signed and Sealed this

Twenty-eighth Day of February, 1989

Attest:

DONALD J. QUIGG

*Attesting Officer*  *Commissioner of Patents and Trademarks*